US008650005B2

(12) United States Patent
Liao

(10) Patent No.: US 8,650,005 B2
(45) Date of Patent: Feb. 11, 2014

(54) SYSTEM AND METHOD FOR THREE-DIMENSIONAL MAXILLOFACIAL SURGICAL SIMULATION AND PLANNING

(75) Inventor: Swanwa Liao, Woodland Hills, CA (US)

(73) Assignee: Dolphin Imaging Systems, LLC, Chatsworth, CA (US)

( * ) Notice: Subject to any disclaimer, the term of this patent is extended or adjusted under 35 U.S.C. 154(b) by 229 days.

(21) Appl. No.: 13/081,869

(22) Filed: Apr. 7, 2011

(65) Prior Publication Data
US 2012/0259592 A1    Oct. 11, 2012

(51) Int. Cl.
    *G06F 17/50*    (2006.01)
(52) U.S. Cl.
    USPC ............................................................. 703/1
(58) Field of Classification Search
    None
    See application file for complete search history.

(56) References Cited

U.S. PATENT DOCUMENTS

| | | | |
|---|---|---|---|
| 5,278,756 A | 1/1994 | Lemchen et al. | 364/413.28 |
| 5,342,202 A | 8/1994 | Deshayes | 434/270 |
| 5,825,941 A | 10/1998 | Linford et al. | 382/294 |
| 7,134,874 B2 | 11/2006 | Chishti et al. | 433/24 |
| 7,234,937 B2 | 6/2007 | Sachdeva et al. | 433/24 |
| 7,953,260 B2 * | 5/2011 | Weinzweig et al. | 382/128 |
| 8,417,004 B2 * | 4/2013 | Liao | 382/128 |
| 2001/0007451 A1 | 7/2001 | Aono | 345/442 |
| 2002/0090123 A1 | 7/2002 | Bazin | 382/128 |
| 2005/0018902 A1 | 1/2005 | Liang | 382/154 |
| 2005/0244794 A1 | 11/2005 | Kemp et al. | 433/217.1 |
| 2006/0215014 A1 | 9/2006 | Cohen et al. | 348/14.08 |
| 2006/0280351 A1 | 12/2006 | Luping et al. | 382/128 |
| 2007/0299551 A1 * | 12/2007 | Weinzweig et al. | 700/90 |
| 2008/0025592 A1 | 1/2008 | Jerebko et al. | 382/132 |
| 2008/0118143 A1 | 5/2008 | Gordon et al. | 382/154 |
| 2008/0285829 A1 | 11/2008 | Wang et al. | 382/131 |
| 2009/0136108 A1 | 5/2009 | Badiei et al. | 382/131 |
| 2010/0145898 A1 * | 6/2010 | Malfliet et al. | 706/47 |

(Continued)

FOREIGN PATENT DOCUMENTS

| | | |
|---|---|---|
| JP | 2001283191 | 10/2001 |
| JP | 2009165558 | 7/2009 |

(Continued)

OTHER PUBLICATIONS

Matching 2-D Ellipses to 3-D Circles with Application to Vehicle to Pose Identification, Marcus Hutter and Nathan Brewer, Canberra, ACT, 0200, Australia, Dec. 2009.*

(Continued)

*Primary Examiner* — Omar Fernandez Rivas
*Assistant Examiner* — Maryam Ipakchi
(74) *Attorney, Agent, or Firm* — Baker Botts L.L.P.

(57) ABSTRACT

A method may include displaying one or more interactive 2D images, each 2D image representing at least bony tissue cranio-facial features of a patient and each 2D image having one or more portions each associated with a corresponding portion of the patient's bony. The method may also include displaying a 3D image representing exterior soft-tissue cranio-facial features of the patient. The method may additionally include receiving input from a user regarding movement of a particular portion of the one or more portions of the 2D image. The method may further include redrawing the 3D image based at least on the movement of the particular portion of the 2D image to simulate response of the exterior soft-tissue cranio-facial features of the patient to movement of a portion of the patient's bony tissue corresponding to the particular portion of the 2D image.

15 Claims, 14 Drawing Sheets

(56) References Cited

U.S. PATENT DOCUMENTS

| | | | |
|---|---|---|---|
| 2011/0045428 A1 | 2/2011 | Boltunov et al. | 433/24 |
| 2011/0194787 A1 | 8/2011 | Chun et al. | 382/284 |
| 2011/0285711 A1 | 11/2011 | Kilgard | 345/426 |
| 2012/0257841 A1 | 10/2012 | Liao | 382/293 |
| 2012/0259592 A1 | 10/2012 | Liao | 703/1 |

FOREIGN PATENT DOCUMENTS

| | | | |
|---|---|---|---|
| WO | WO 99/59106 | 11/1999 | G06T 15/00 |
| WO | WO 9959106 A1 * | 11/1999 | G06T 15/00 |
| WO | WO 01/80765 | 11/2001 | |
| WO | WO 02/03304 | 1/2002 | G06F 19/00 |
| WO | WO 2005/025404 | 3/2005 | |

OTHER PUBLICATIONS

International Search Report and Written Opinion; Application No. PCT/ES2011/070133; pp. 10, Nov. 24, 2011.

Xia et al.; "Three-dimensional Virtual Reality Surgical Planning and Simulation Workbench for Orthognathic Surgery"; Int J Adult Orthod Orthognath Surg, vol. 15, No. 4; pp. 265-282, 2000.

James L. Ackerman et al., "Soft Tissue Limitations in Orthodontics: Treatment Planning Guidelines", vol. 67 No. 5 1997, pp. 327-336.

United States Office Action; U.S. Appl. No. 13/081,895; pp. 12, Sep. 4, 2012.

International Search Report and Written Opinion; PCT/US2012/031942; pp. 11, Oct. 4, 2012.

International Search Report and Written Opinion; PCT/US2012/031945; pp. 8, Oct. 4, 2012.

Hwang et al.; "Maxillocfacial 3-dimensional image analysis for the diagnosis of facial asymmetry"; American Journal of Orthodontics and Dentofacial Orthopedics; 130 (6); 779-785, (2006).

Xia at al.; "Computer-assisted three-dimensional surgical planning and simulation"; Int. J. Oral Maxillofac. Surg.; vol. 29; pp. 250-258, (2000).

International Preliminary Report on Patentability; PCT/US2012/031942; pp. 5, Oct. 17, 2013.

International Preliminary Report on Patentability; PCT/US2012/031945; pp. 5, Oct. 17, 2013.

* cited by examiner

SYSTEM AND METHOD FOR THREE-DIMENSIONAL MAXILLOFACIAL SURGICAL SIMULATION AND PLANNING

TECHNICAL FIELD

The present disclosure relates in general to dentofacial imaging, and more particularly to systems and methods for surgical planning using dentofacial imaging.

BACKGROUND

Dentofacial surgery, also referred to as oral and maxillofacial surgery, is often employed to correct a wide spectrum of diseases, injuries and defects in the head, neck, face, jaws and the hard and soft tissues of the oral and maxillofacial region of humans or other non-human patients. As capabilities of computers and software improve, practitioners of dentofacial surgery increasingly use computer-aided dentofacial imaging tools in order to model dentofacial features of patients, diagnose diseases, injuries, and defects, plan dentofacial surgical procedures and other treatments, and educate patients regarding diagnoses and treatments.

For example, to plan and simulate a dentofacial surgery, a practitioner may, with the aid of a computer-aided tool, virtually modify various bones or bone segments of the patient via a user interface of a computer. Such computer-aided planning and simulation may allow a practitioner to simulate effect of various surgical adjustments on a patient, including effects on a patient's aesthetic appearance. However, traditional computer-aided surgical planning and simulation tools have significant disadvantages. For example, digital images of a patient's facial tissues generated by imaging devices may include undesirable noise and other artifacts. Thus, many traditional planning and simulation tools allow a practitioner to perform "cleaning" of a digital image to remove noise from the image. However, such cleaning of noise is complicated due to the non-linear and three-dimensional shapes of the tissues comprising a human head. As another example, traditional planning and simulation tools typically allow a practitioner to make two-dimensional surgical adjustments of bone and generate a simulated two-dimensional soft-tissue response based on such adjustments, which does not allow the practitioner to view a three-dimensional model of the soft-tissue response.

SUMMARY

In accordance with the teachings of the present disclosure, disadvantages and problems associated with traditional approaches to surgical planning using dentofacial imaging may be substantially reduced or eliminated.

In accordance with embodiments of the present disclosure, a method may include displaying one or more interactive two-dimensional images, each two-dimensional image representing at least bony tissue cranio-facial features of a patient and each two-dimensional image having one or more portions each associated with a corresponding portion of the patient's bony tissue such that a user may, via a user input device, cause movement of at least one of the one or more portions of such two-dimensional image to simulate movement of the corresponding portion of the patient's bony tissue in an osteotomy procedure. The method may also include displaying a three-dimensional image representing exterior soft-tissue cranio-facial features of the patient. The method may additionally include receiving input from a user regarding movement of a particular portion of the one or more portions of the two-dimensional image. The method may further include redrawing the three-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image.

In accordance with additional embodiments of the present disclosure, an article of manufacture may include a non-transitory computer-readable medium and computer-executable instructions carried on the computer-readable medium, the instructions executable by one or more processors and configured to cause the one or more processors to: (i) display one or more interactive two-dimensional images, each two-dimensional image representing at least bony tissue cranio-facial features of a patient and each two-dimensional image having one or more portions each associated with a corresponding portion of the patient's bony tissue such that a user may, via a user input device, cause movement of at least one of the one or more portions of such two-dimensional image to simulate movement of the corresponding portion of the patient's bony tissue in an osteotomy procedure; (ii) display a three-dimensional image representing exterior soft-tissue cranio-facial features of the patient; (iii) receive input from a user regarding movement of a particular portion of the one or more portions of the two-dimensional image; and (iv) redraw the three-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image.

In accordance with further embodiments of the present disclosure, a computing system may include a processor and a memory communicatively coupled to the processor and having stored thereon a program of instructions configured to, when executed by the processor: (i) display one or more interactive two-dimensional images, each two-dimensional image representing at least bony tissue cranio-facial features of a patient and each two-dimensional image having one or more portions each associated with a corresponding portion of the patient's bony tissue such that a user may, via a user input device, cause movement of at least one of the one or more portions of such two-dimensional image to simulate movement of the corresponding portion of the patient's bony tissue in an osteotomy procedure; (ii) display a three-dimensional image representing exterior soft-tissue cranio-facial features of the patient; (iii) receive input from a user regarding movement of a particular portion of the one or more portions of the two-dimensional image; and (iv) redraw the three-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image.

In accordance with additional embodiments of the present disclosure, a method may include mapping an ellipse with its center at the origin of an xy-coordinate plane to a circle with its center at the origin of the xy-coordinate plane. The method may also include transforming a three-dimensional subject image including a curved profile in the xy-coordinate plane to an intermediate image based at least on the mapping of the ellipse to a base circle. The method may further include transforming the intermediate image to a transformed image having a linear profile by distorting each of one or more points of interest of the intermediate image based at least on a dimension of the circle and a coordinate of such point.

In accordance with further embodiments of the present disclosure, an article of manufacture may include a non-transitory computer-readable medium and computer-executable instructions carried on the computer-readable medium, the instructions executable by one or more processors and configured to cause the one or more processors to: (i) map an ellipse with its center at the origin of an xy-coordinate plane to a circle with its center at the origin of the xy-coordinate plane; (ii) transform a three-dimensional subject image including a curved profile in the xy-coordinate plane to an intermediate image based at least on the mapping of the ellipse to a base circle; and (iii) transform the intermediate image to a transformed image having a linear profile by distorting each of one or more points of interest of the intermediate image based at least on a dimension of the circle and a coordinate of such point.

In accordance with another embodiment of the present disclosure, a computing system may include a processor and a memory communicatively coupled to the processor and having stored thereon a program of instructions configured to, when executed by the processor: (i) map an ellipse with its center at the origin of an xy-coordinate plane to a circle with its center at the origin of the xy-coordinate plane; (ii) transform a three-dimensional subject image including a curved profile in the xy-coordinate plane to an intermediate image based at least on the mapping of the ellipse to a base circle; and (iii) transform the intermediate image to a transformed image having a linear profile by distorting each of one or more points of interest of the intermediate image based at least on a dimension of the circle and a coordinate of such point.

Other technical advantages will be apparent to those of ordinary skill in the art in view of the following specification, claims, and drawings.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

FIGS. 1A, 1B and 2A-2D depict an example user interface screen 400 of a computer-aided surgical planning tool, in accordance with embodiments of the present disclosure. In particular, user interface screen 400 may be displayed to a user to assist a user to "clean" an image of the anatomy of a patient. For example, to effectively plan a surgery, a user may desire to remove image artifacts caused by noise in an imaging device. As another example, a user may desire to crop certain anatomical structures (e.g., orthodontic braces, teeth, etc.) such that the resulting image depicts desired anatomical structures.

Figure 1A:
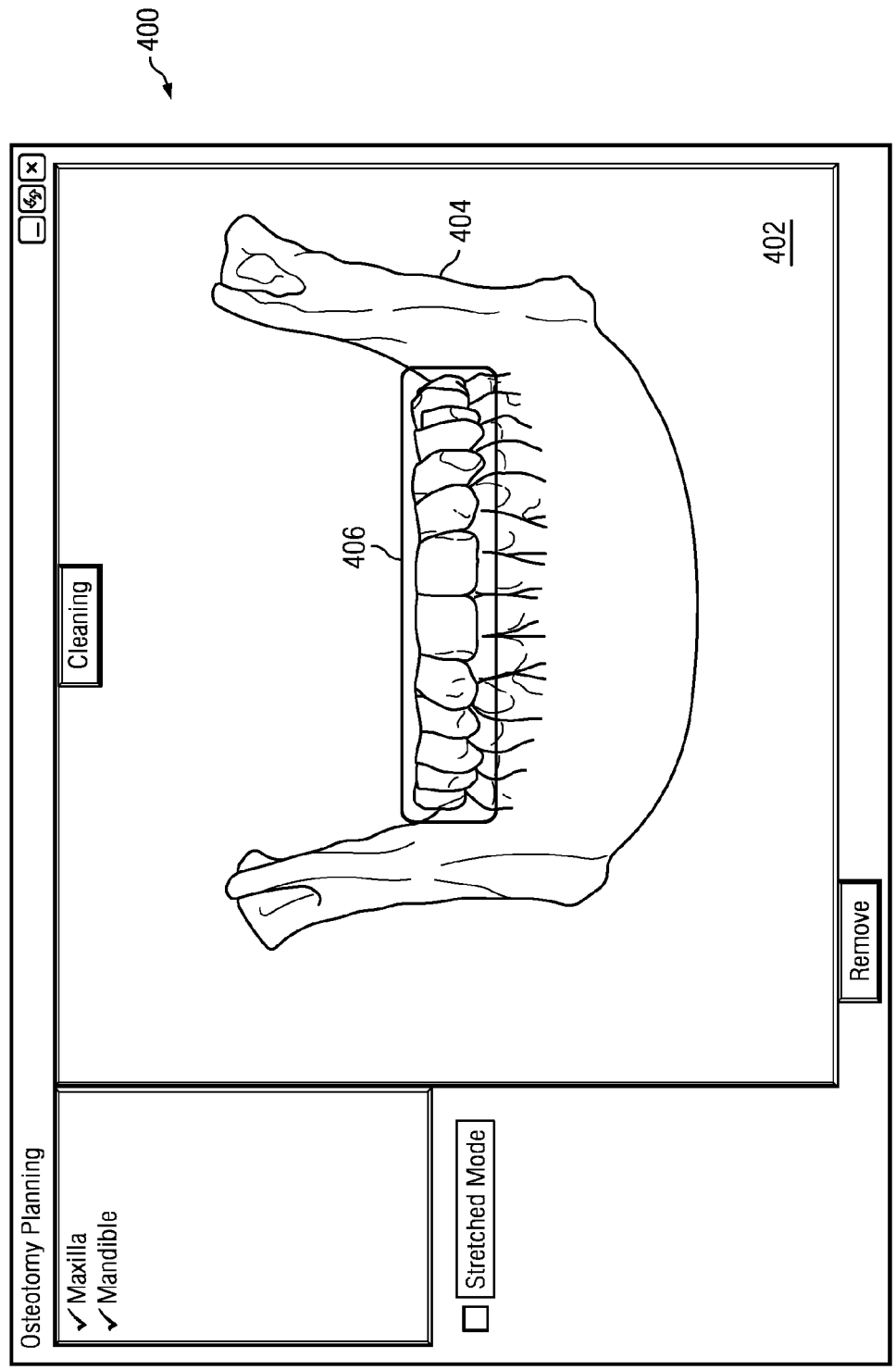
FIGS. 1A, 1B and 2A-2D depict another example user interface screen of a computer-aided surgical planning tool, in accordance with embodiments of the present disclosure.
Figure 1B:
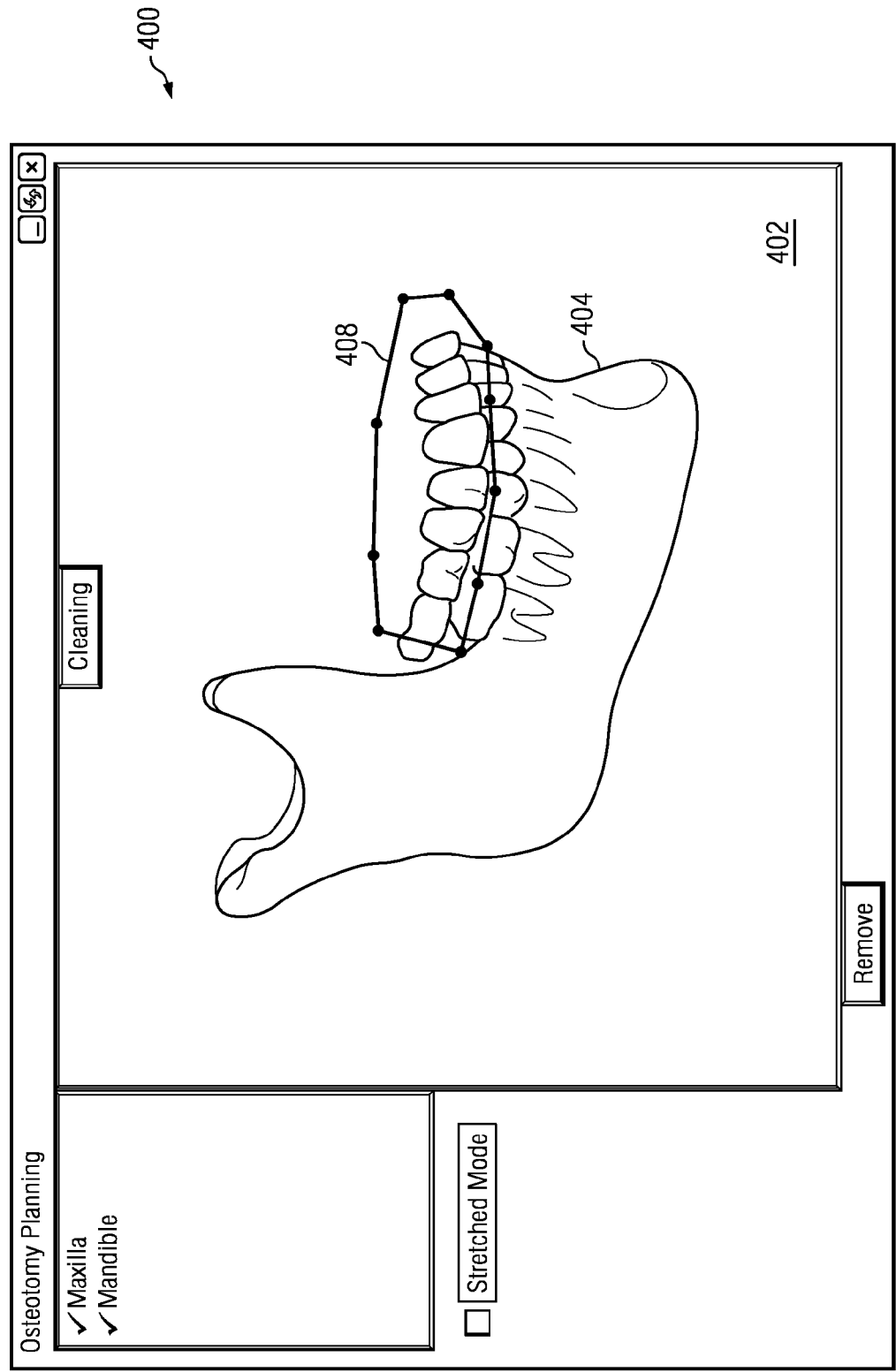

To illustrate, user interface screen 400 of FIGS. 1A and 1B includes two different views of a segmented surface image 402 of a patient mandible 404. Segmented surface image 402 may depict the outer surface of a particular portion of a patient's anatomy and may be generated in any suitable manner. For example, in some embodiments, the computer-aided surgical planning tool may generate segmented surface image 402 based on data produced by imaging the patient using radiography or other medical imaging. The computer-aided surgical tool may also allow a user to manipulate segmented surface image 402 to obtain different views of segmented surface image 402. As an example, a user may, via one or more user interface devices (e.g., mouse, keyboard, etc.), input actions or commands to display a different view of segmented surface image 402 (e.g., rotate from the view in FIG. 1A to the view in FIG. 1B) allowing a user various perspectives of the three-dimensional segmented surface image 402. The computer-aided surgical tool may also allow a user to perform other actions upon segmented surface image 402, including selecting and removing undesired portions of segmented surface image 402.

To illustrate, in FIGS. 1A and 1B, segmented surface image 402 includes not only a patient mandible 404 and lower teeth of such mandible 404, but also the patient's upper teeth, which a user may desire to crop from image 402. However, the curved nature of the patient mandible may render selection and deletion of undesired features difficult. For example, if a user selects the upper row of teeth of an anterior view of mandible 404 as indicated by selection 406 in FIG. 1A, selection 406 may overlap other features of mandible 404 that the user desires to retain in image 402. Thus, deletion of such selection 406 may undesirably delete such features. As another example, if the user selects the upper row of teeth of a right-side lateral view of mandible 404 as indicated by selection 408 in FIG. 1B, selection 408 may overlap features on the left side of mandible 404 that the user desires to retain in image 402, and deletion of such selection 408 may undesirably delete such features.

Figure 2A:
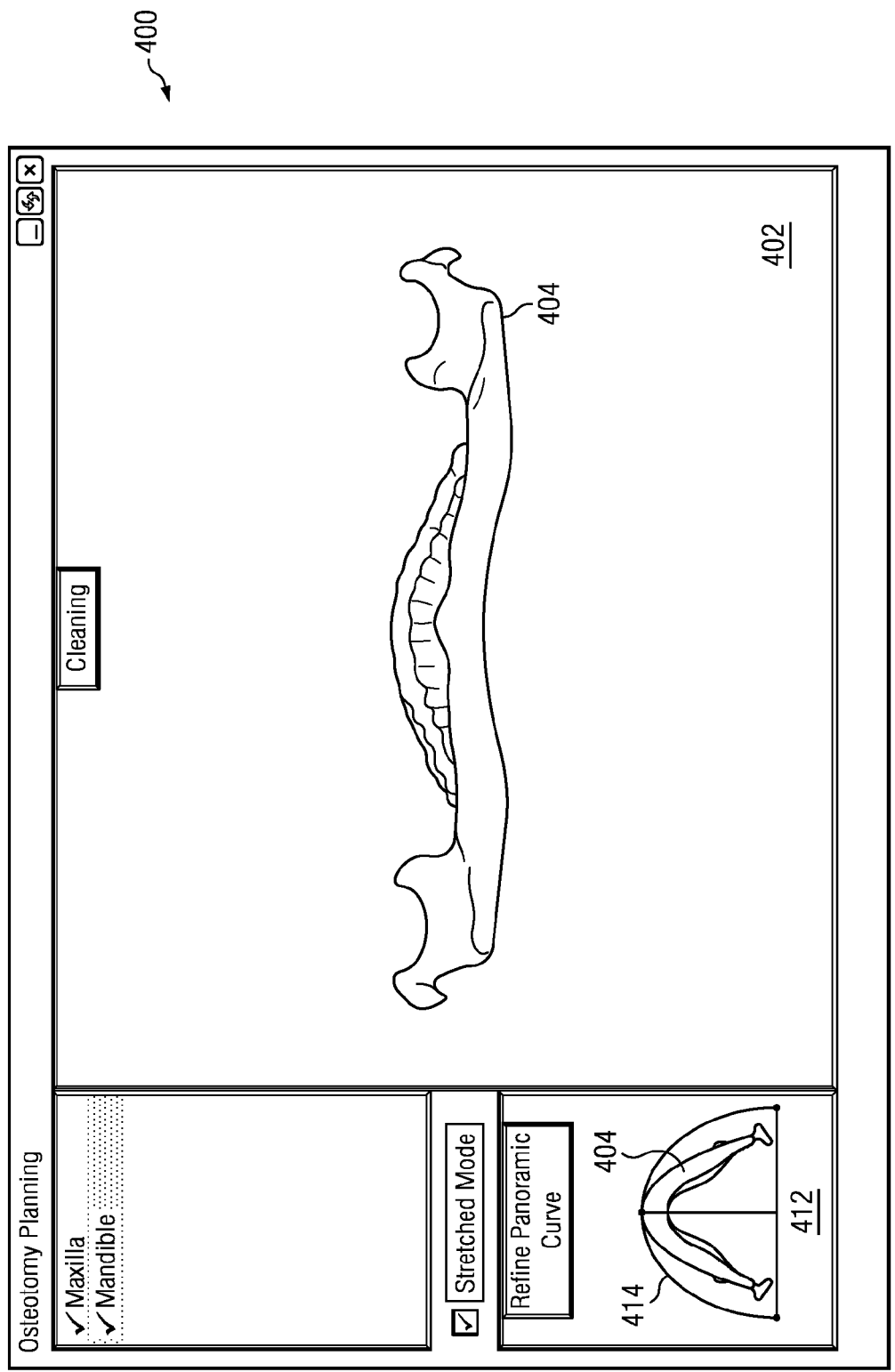
Figure 2B:
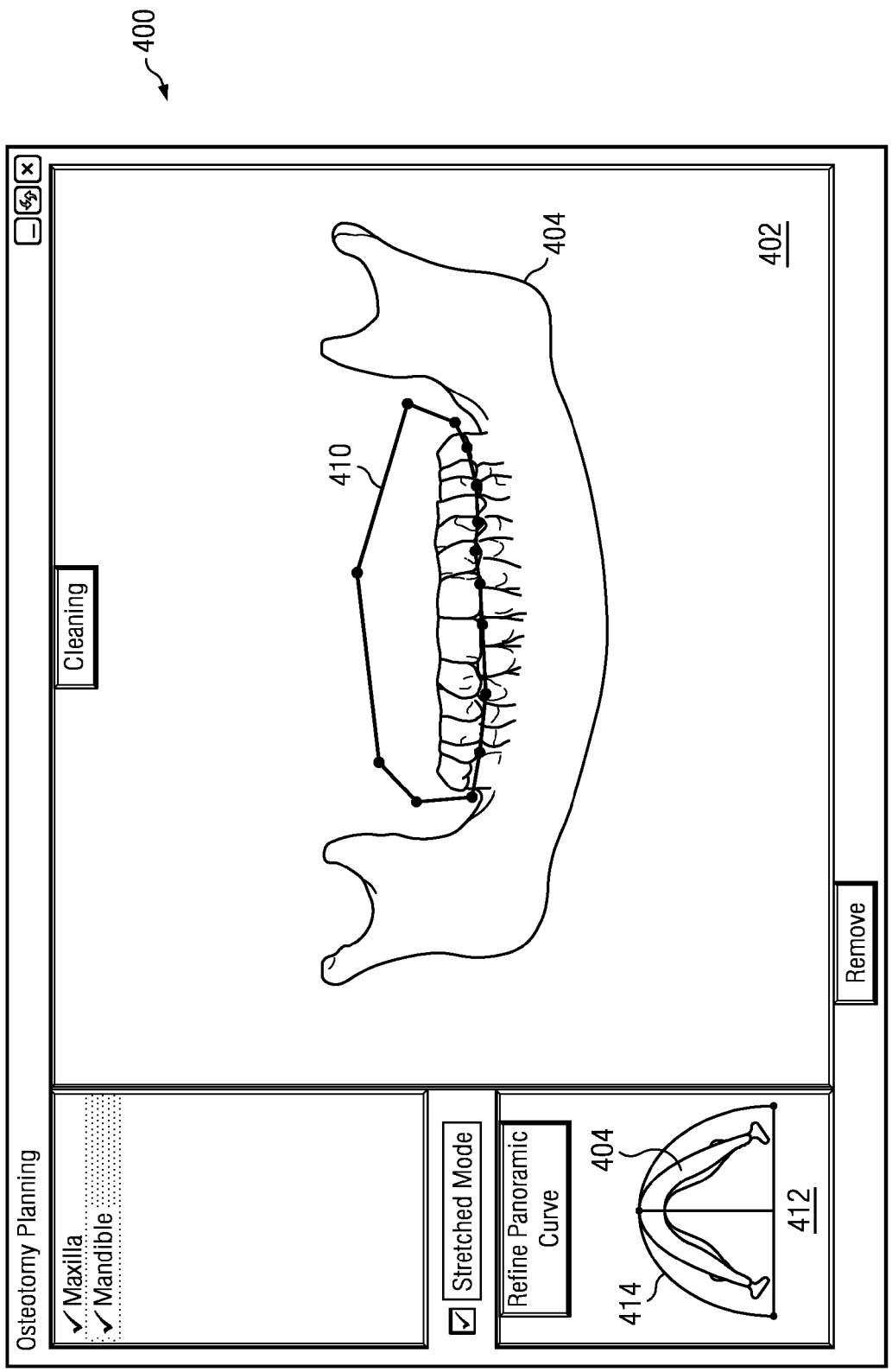
Figure 2C:
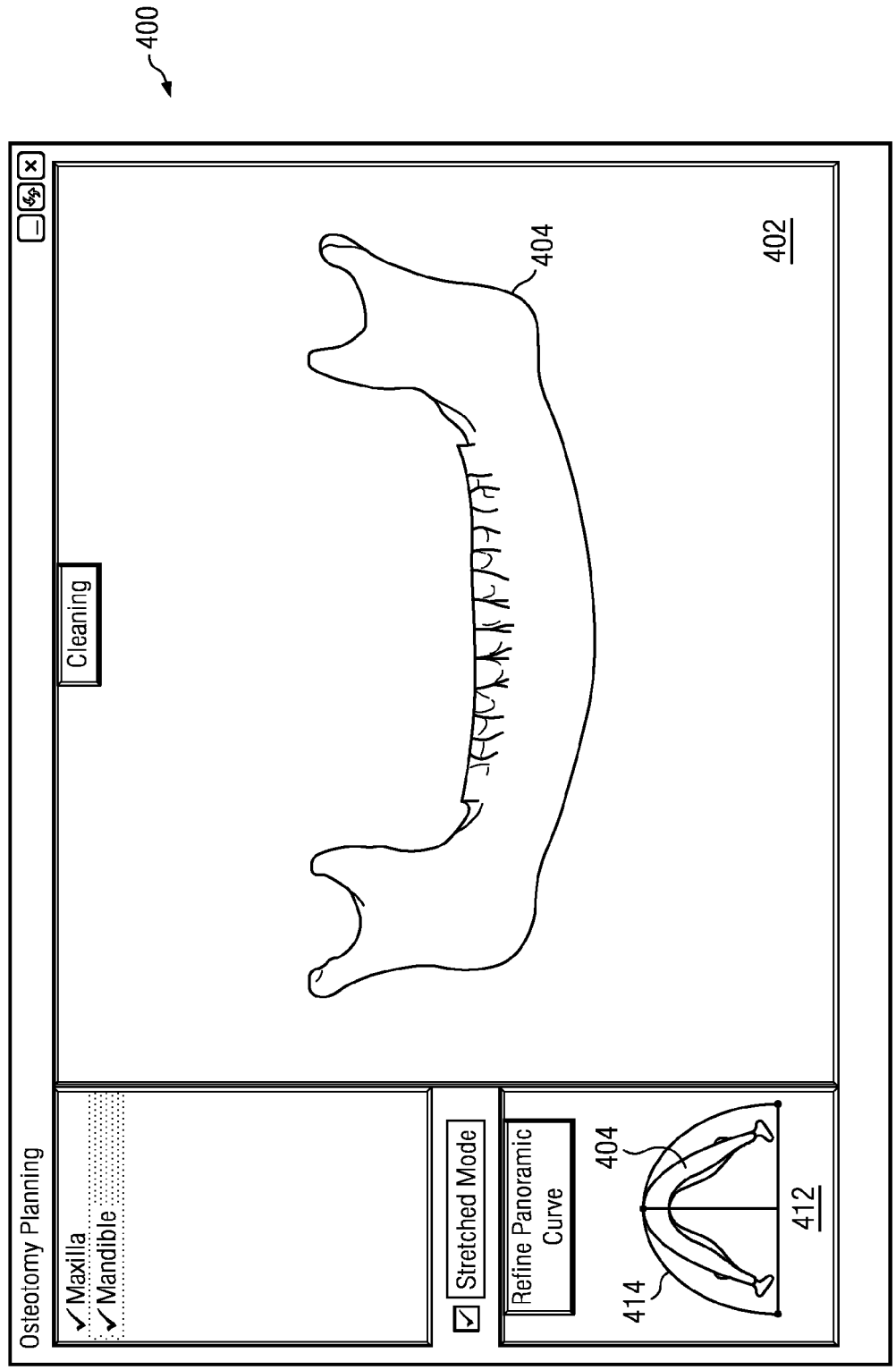
Figure 2D:
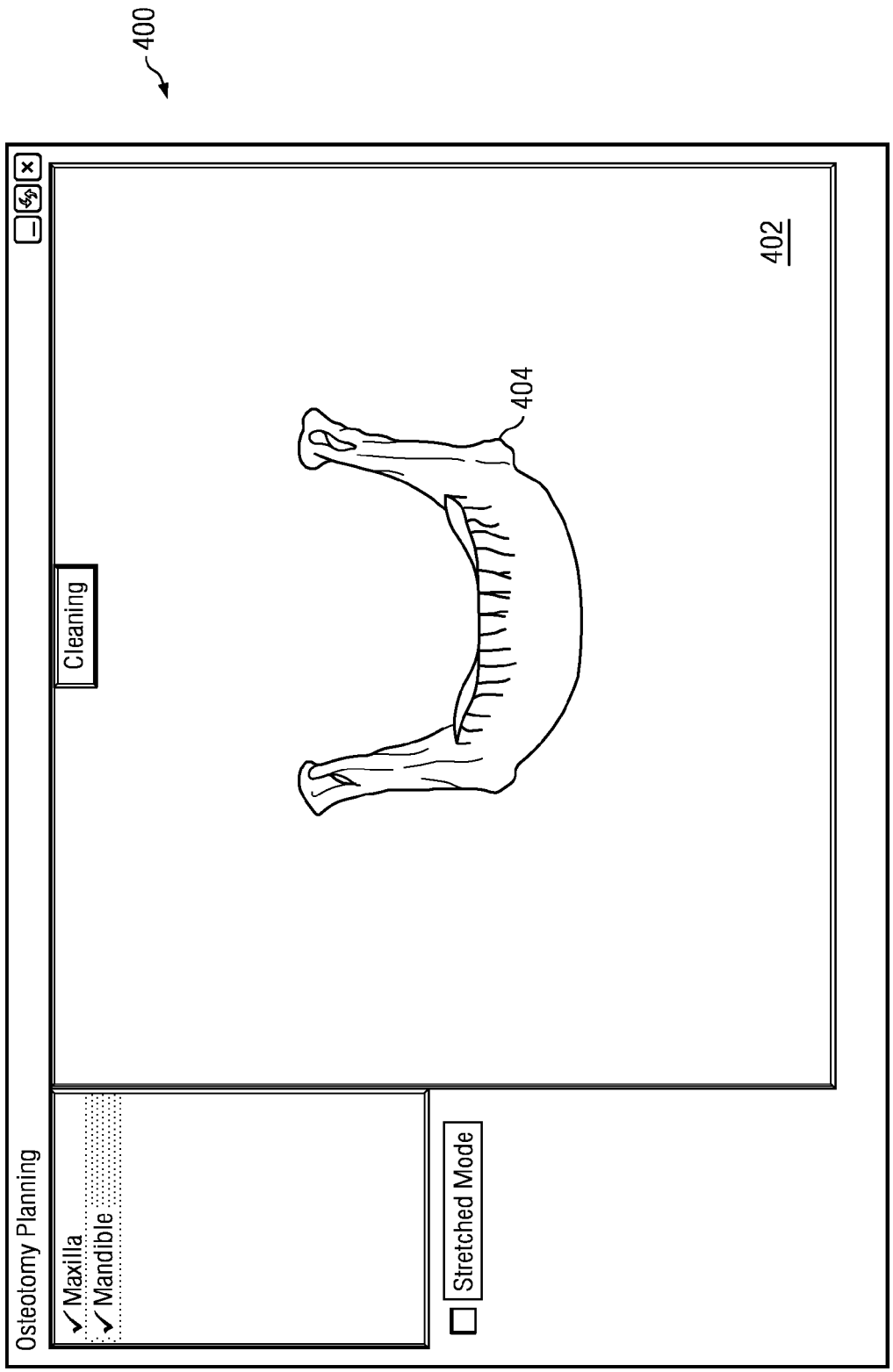

To reduce or eliminate such disadvantages, the computer-aided surgical planning tool may allow a user to input an action or command (e.g., by using a mouse or other pointing device to check the check box labeled "Stretched Mode" in interface screen 400) to transform the representation of mandible 404 in image 402 such that the curved mandible is warped to a linear shape, as depicted in FIG. 2A (inferior view of mandible 404) and 2B (anterior view of mandible 404). In some embodiments, such transformation may be made such that points representing the surface of mandible 404 are translated only in a latitudinal direction (e.g., remain at the same height). With such representation, a user may select the upper row of teeth, as indicated by selection 410, and delete such selection 410, as shown in FIG. 2C. Accordingly, the features that the user desires to retain are less likely to be deleted, as the linear representation of mandible 404 may reduce or avoid the deletion of other features behind the teeth to be removed from image 402. FIG. 2D depicts an anterior view of mandible 404 after the linearization of mandible 404 and selection and deletion of the upper row of teeth as shown in FIGS. 2A-2C.

Although FIGS. 1A, 1B, and 2A-2D depict linearization of an image of a human mandible, similar techniques may be used for linearization of any other three-dimensional image having a curved feature (e.g., a maxilla).

Figure 3:
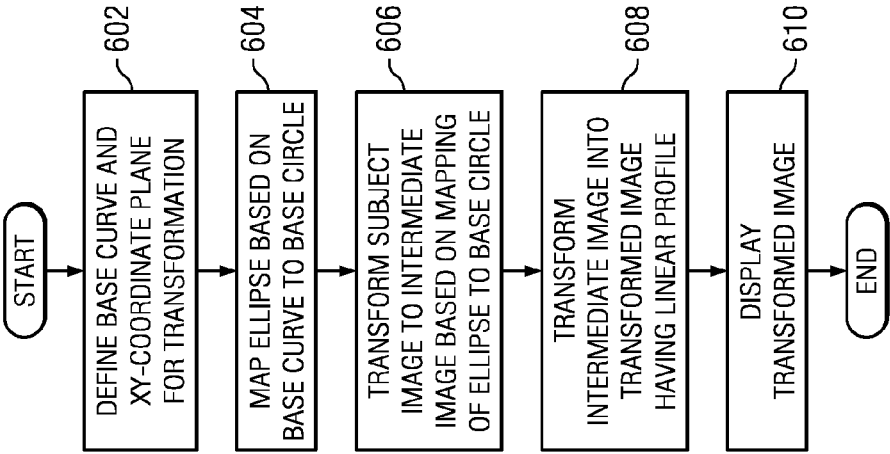
FIG. 3 is a flow chart depicting an example method for transformation of a three-dimensional image with a curved profile to a three-dimensional linear profile, in accordance with embodiments of the present disclosure.

FIG. 3 is a flow chart depicting an example method 600 for transformation of a three-dimensional image with a curved profile to a three-dimensional linear profile, in accordance with embodiments of the present disclosure. For example, the steps of FIG. 3 may be employed to transform an image of a mandible or maxilla from its natural curved shape to a linear shape. Method 600 may be performed by a computer-aided surgical planning tool, or any other suitable executable program of instructions embodied on a computer-readable medium.

At step 602, computer-aided surgical planning tool and/or a user thereof may define a base curve 414 and xy-coordinate plane for the three-dimensional image to be transformed. For example, as depicted in FIGS. 2A-2C, the computer-aided surgical planning tool may display a pane 412 permitting a user to interactively define base curve 414 as a semi-ellipse having a desired minor radius and major radius. In addition, the computer-aided surgical planning tool may overlay a view of the three-dimensional image (e.g., maxilla, mandible) perpendicular to the curved profile of the subject image to be transformed in pane 412, which may provide the user a guide for defining dimensions of base curve 414. Furthermore, base curve 414 may define an xy-coordinate plane (e.g., wherein the base of the semi-ellipse of base curve 414 may comprise the x-axis) and the alignment of the view of the three-dimensional image relative to the base curve may define the locations of points of the image in such xy-coordinate system.

Figure 4:
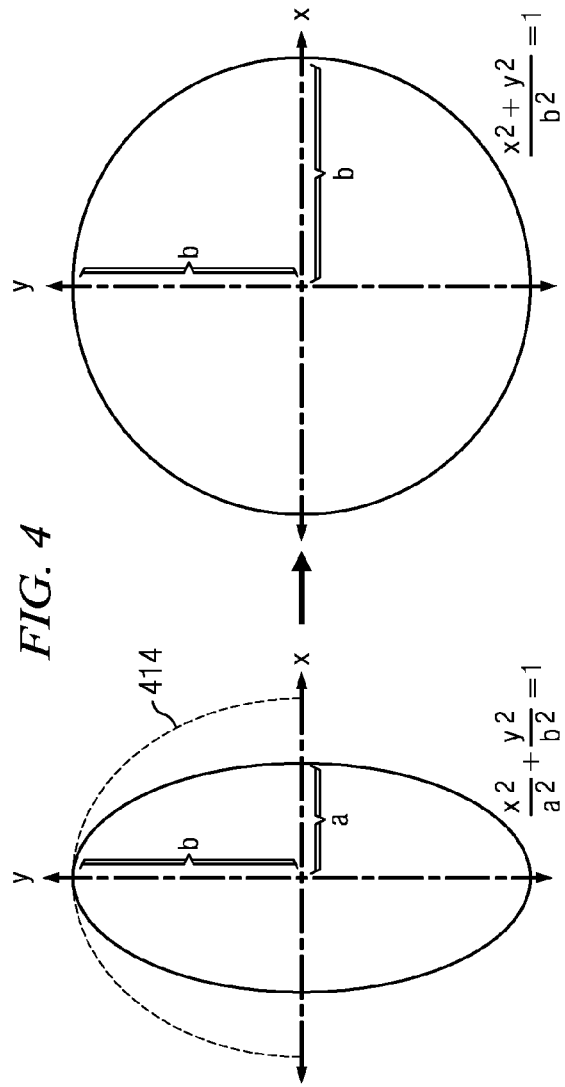
FIGS. 4-6 depict graphical representations of various steps for transformation of a three-dimensional image with a curved profile to a three-dimensional linear profile, in accordance with embodiments of the present disclosure.

At step 604, computer-aided surgical planning tool may map an ellipse having its minor radius a and major radius b equal to that of the semi-ellipse of the base curve 414 to a base circle having its origin at the center of the origin or the xy-plane. The base circle may have a radius equal to the minor radius of the ellipse, the major radius of the ellipse, or some other radius. An example of such mapping is illustrated in FIG. 4, with the base circle having a radius equal to b, the major radius of the ellipse.

Figure 5:
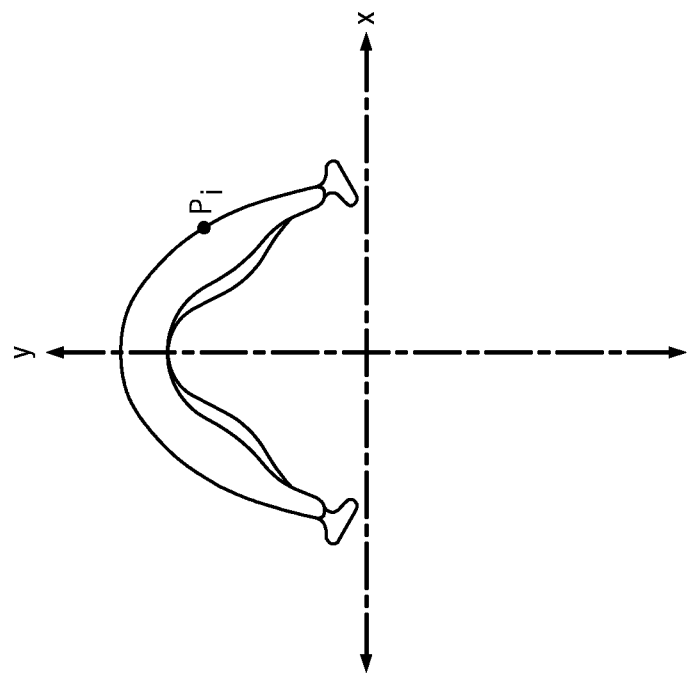
Figure 5:
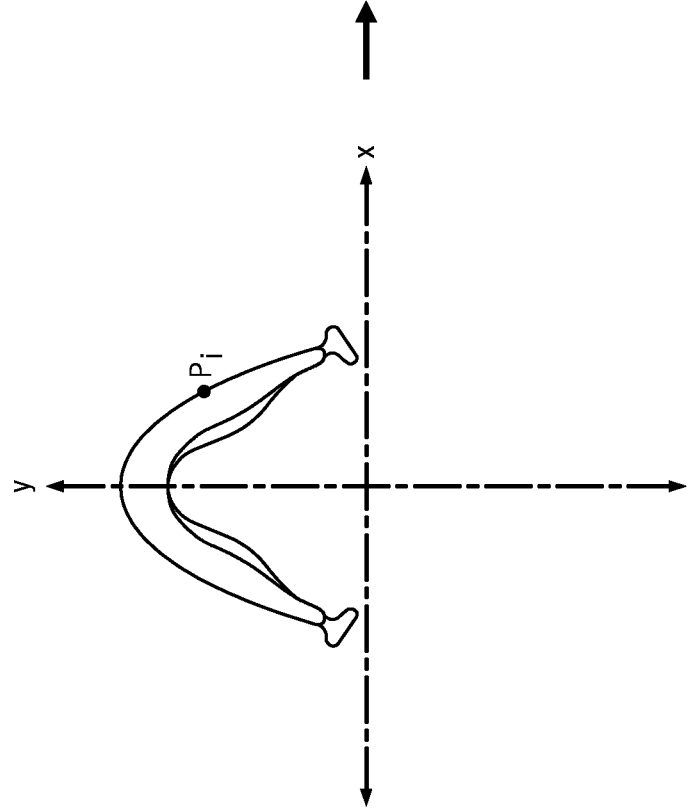

At step 606, computer-aided surgical planning tool may perform a first transformation transforming the subject image to an intermediate image based on the mapping of the ellipse defined by base curve 414 to the base circle. To illustrate, the image to be transformed may be a segmented surface image, which is defined by a plurality of points in three-dimensional space (e.g., x, y, and z coordinates) which serve as end points of a plurality of triangles that form the segmented surface. If the z-axis of such coordinate system is substantially perpendicular to a view of the curved profile of the image (e.g., perpendicular to the superior or inferior view of a maxilla or mandible), then the z-coordinate of each point $P_i$ of the segmented surface image may remain the same value during this first transformation. In addition, the y-coordinate of each point $P_i$ may also stay the same as the ellipse defined by the base curve may be "stretched" to the base circle in the x-axis only. Accordingly, only the x-coordinates of each point $P_i$ may be modified in the first transformation, and may be modified according to the following equations (assuming the base circle has a radius equal to the major radius of the base ellipse):

$$P_x' = P_x \times b/a$$

$$P_y' = P_y$$

$$P_z' = P_z$$

where $P_x$, $P_y$, and $P_z$ are respectively the x, y, and z coordinates of each point $P_i$ in the image to be transformed, $P_x'$, $P_y'$, and $P_z'$ are respectively the x, y, and z coordinates of each corresponding point $P_i'$ in the intermediate image, a is the minor radius of base curve 114, and b is the radius of the circle and the major radius of base curve 114. FIG. 5 illustrates this first transformation in the xy-plane.

Figure 6:
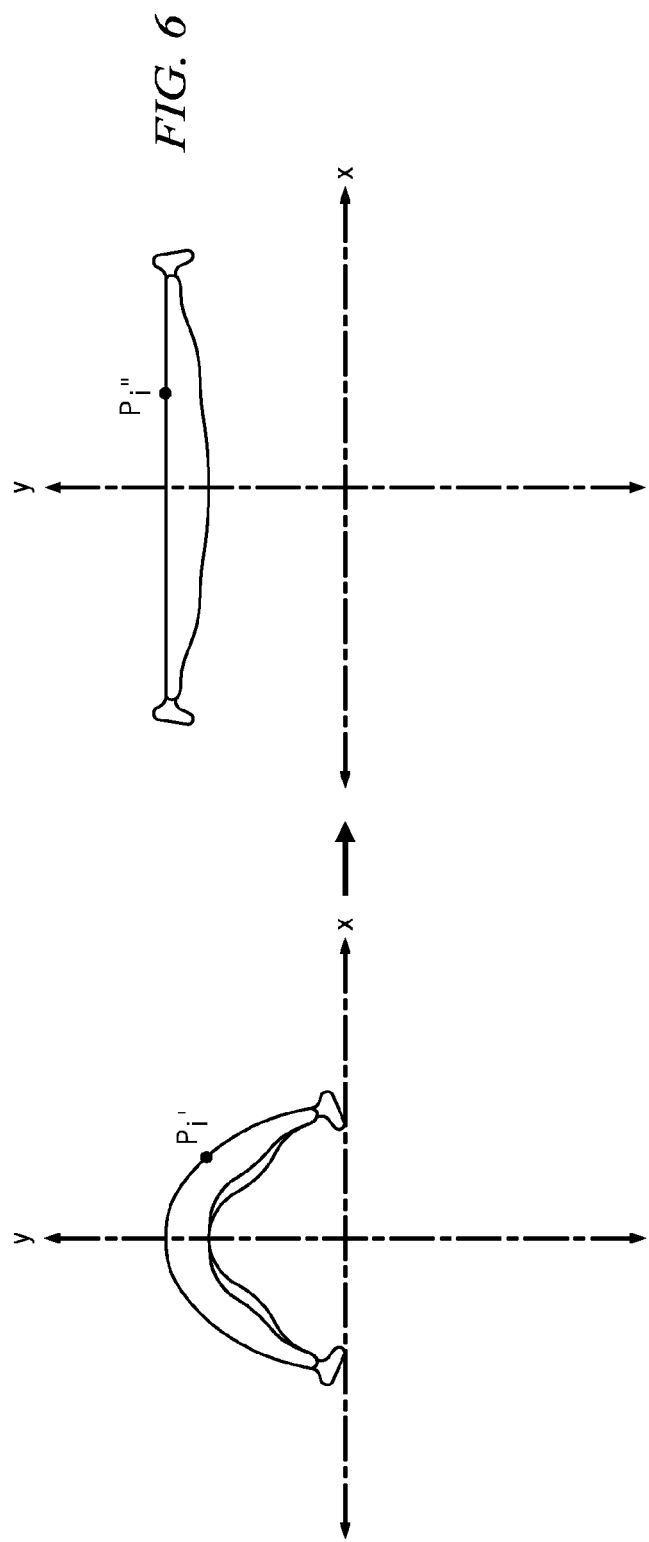

At step 608, computer-aided surgical planning tool may perform a second transformation transforming the intermediate image to a transformed image with the curved profile of the subject image transformed into a linear profile. In the transformation, each point of interest in the intermediate image (e.g., each point of a segmented surface image) may be modified according to the following equations:

$$P_x'' = b \times \arctan(P_x'/P_y')$$

$$P_y'' = \sqrt{(P_x'^2 + P_y'^2)}$$

$$P_z'' = P_z'$$

where $P_x''$, $P_y''$, and $P_z''$ are respectively the x, y, and z coordinates of each point $P_i''$ in the transformed image, $P_x'$, $P_y'$, and $P_z'$ are respectively the x, y, and z coordinates of each corresponding point $P_i'$ in the intermediate image, and b is the radius of the circle and the major radius of base curve 114. FIG. 6 illustrates this second transformation in the xy-plane.

At step 610, the computer-aided surgical planning tool may display the transformed image (e.g., to a display as shown in FIG. 2A or 2B). After completion of step 610, method 600 may end.

Although FIG. 3 discloses a particular number of steps to be taken with respect to method 600, it is understood that method 600 may be executed with greater or lesser steps than those depicted in FIG. 3. In addition, although FIG. 3 discloses a certain order of steps to be taken with respect to method 600, the steps comprising method 600 may be completed in any suitable order.

Figure 12:
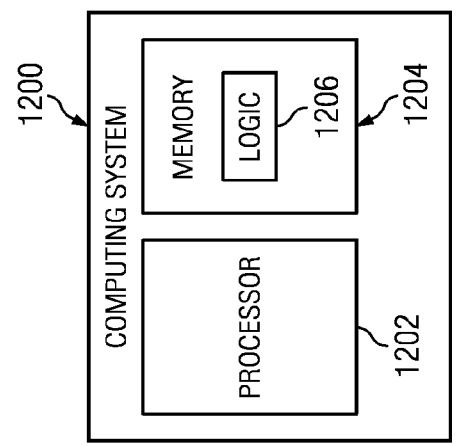
FIG. 12 depicts a block diagram of an example computing system, in accordance with embodiments of the present disclosure.

Method 600 may be implemented using system operable to implement method 600, including without limitation, computer system 1200 depicted in FIG. 12. In certain embodiments, method 600 may be implemented partially or fully in software embodied in computer-readable media.

After an image has been transformed, a user of the computer-aided surgical planning tool may, via a user interface, "clean" undesired artifacts from an image (e.g., by selecting undesired artifacts and deleting such selections). Following such cleaning, a user may desire to transform the transformed image back into an image with a curved profile. Accordingly, the computer-aided surgical planning tool may transform the image back into a cleaned imaged with a curved profile by applying the inverse calculations of those applied above to various points of interest in the transformed image.

Figure 7:
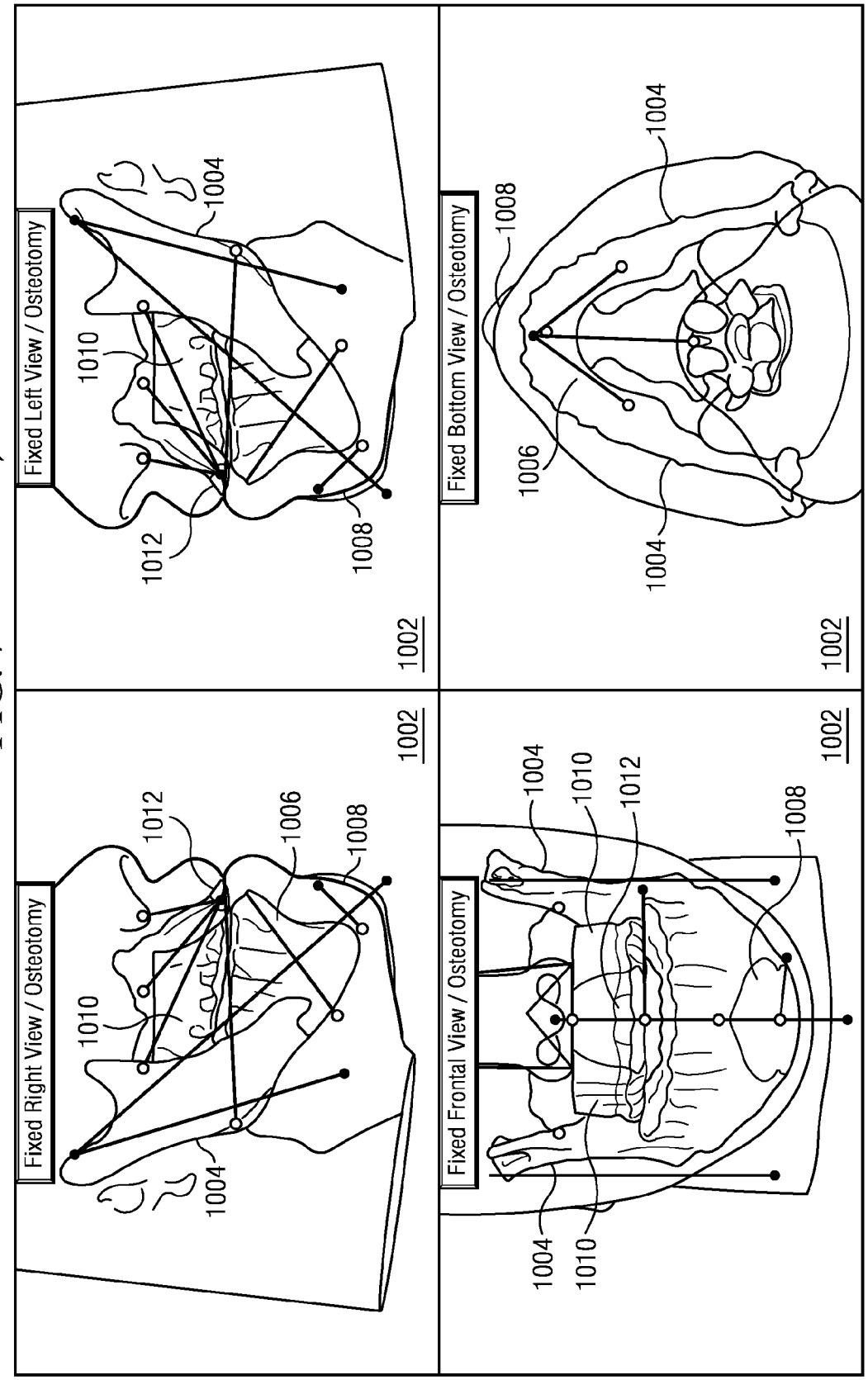
FIGS. 7 and 9 depict other example user interface screens of a computer-aided surgical planning tool, in accordance with embodiments of the present disclosure.

FIG. 7 depicts an example user interface screen 1000 of a computer-aided surgical planning tool, in accordance with embodiments of the present disclosure. User interface screen 1000 may facilitate a user's planning of an osteotomy procedure, simulating soft tissue response of a patient to movements of bony tissue below the soft tissue. As shown in FIG. 7, user interface screen 1000 may include one or more panes 1002 depicting a two-dimensional view of a patient's craniofacial features, including bony tissue and soft tissue. Images depicted in such views may be created by the computer-aided surgical planning tool or other program of instructions based on a radiograph or other image of the tissues of an individual's head.

Figure 8:
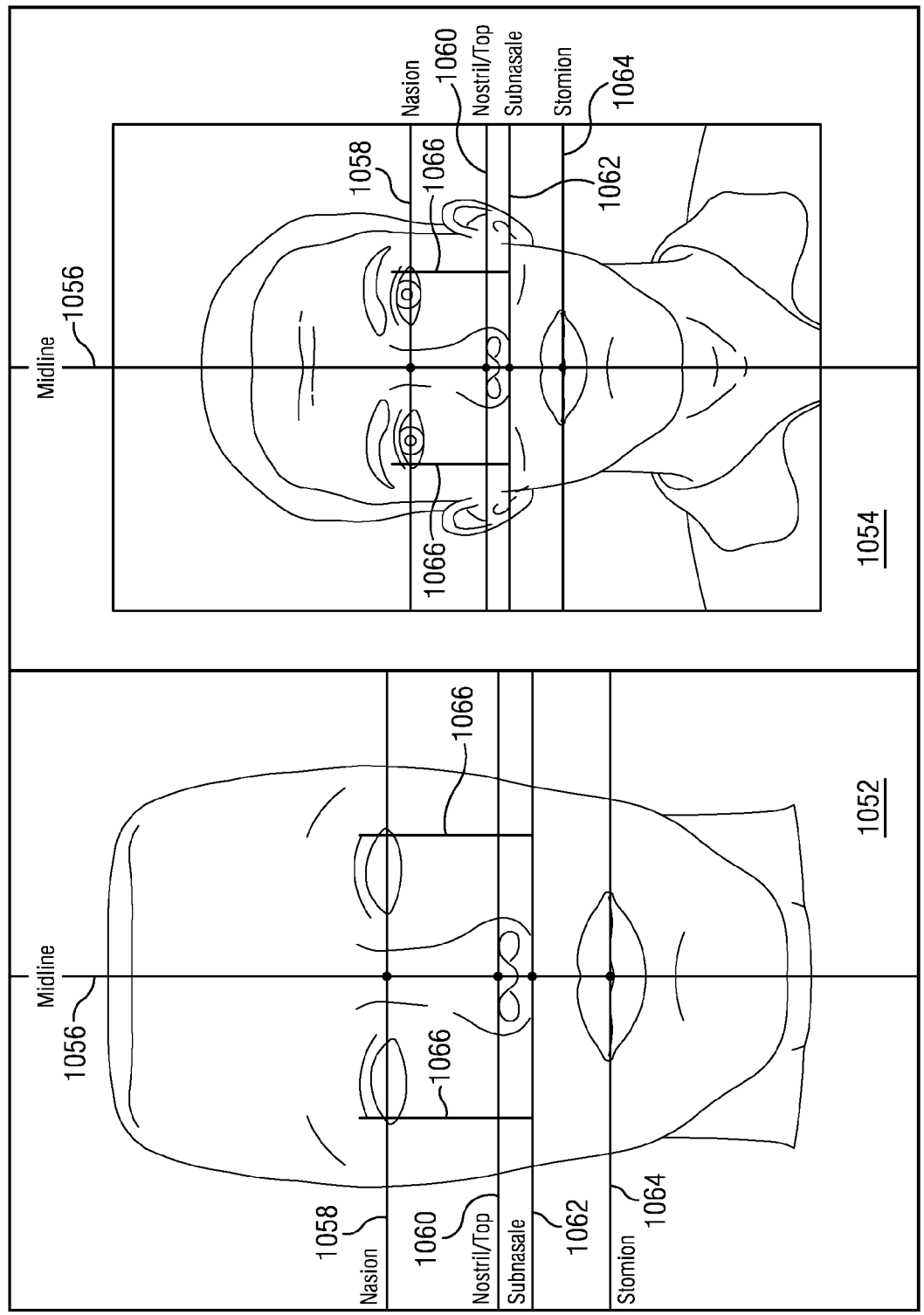
FIG. 8 depicts a three-dimensional image of a patient's soft tissue and a two-dimensional image of a patient's soft tissue, including particular landmarks of the patient's face on each of the images.

As shown in FIG. 7, the computer-aided surgical planning tool may depict soft tissues of the cranio-facial features as partially transparent in panes 1002, allowing bony tissue to be seen under the overlaying soft tissues. In certain embodiments, computer-aided surgical planning tool may allow a user to vary the opacity or transparency of the soft tissues. In addition, the computer-aided surgical planning tool may load a photograph or other image depicting superficial features of the patient's face, and overlay and contour such image over the various views depicted in panes 1002, allowing surgical simulation of the response of superficial facial features to movement of bony tissue in an osteotomy. For example, a three-dimensional camera may be used to capture an image of a patient's facial surface, and such three-dimensional facial surface image may be superimposed upon the image of the soft tissues, according to known techniques. As another example, one or more two-dimensional facial images may be used to capture images of a patient's facial surfaces, and such two-dimensional images may be wrapped onto the surface of the three-dimensional image of the patient's soft tissue, as illustrated in FIG. 8. FIG. 8 depicts a three-dimensional image of a patient's soft tissue 1052 and a two-dimensional image of a patient's superficial facial features 1054, including particular landmarks 1056, 1058, 1060, 1062, 1064, and 1066 of the patient's face on each image 1052 and 1054. For example, a computer-aided surgical planning tool may present to a user a user interface similar to that depicted in FIG. 8, and a user may, via the user interface, identify corresponding features in each of the soft tissue image 1052 and superficial facial feature image 1054. For example, the user may identify, without limitation, midline 1056, nasion line 1058, nostril top line 1060, subnasale line 1062, stomion line 1064, and edge of eye lines 1066. Similar landmark identifications can be made to other two-dimensional images of a patient's superficial features, and such two-dimensional images may be superimposed over the three-dimensional soft tissue volume image according to known techniques.

Returning to FIG. 7, the computer-aided surgical planning tool may allow a user to define various cuts of a patient's maxilla and mandible, thus defining portions of bony tissue that may be moved during an osteotomy (e.g., mandibular ramuses 1004, mandible body 1006, chin 1008, maxilla sides 1010, and maxilla front 1012), and allowing the user (e.g., via commands or actions input via keyboard, mouse, or other device) to simulate such movements using the computer-aided surgical planning tool by translating and/or rotating such various portions of bony tissue.

Figure 9:
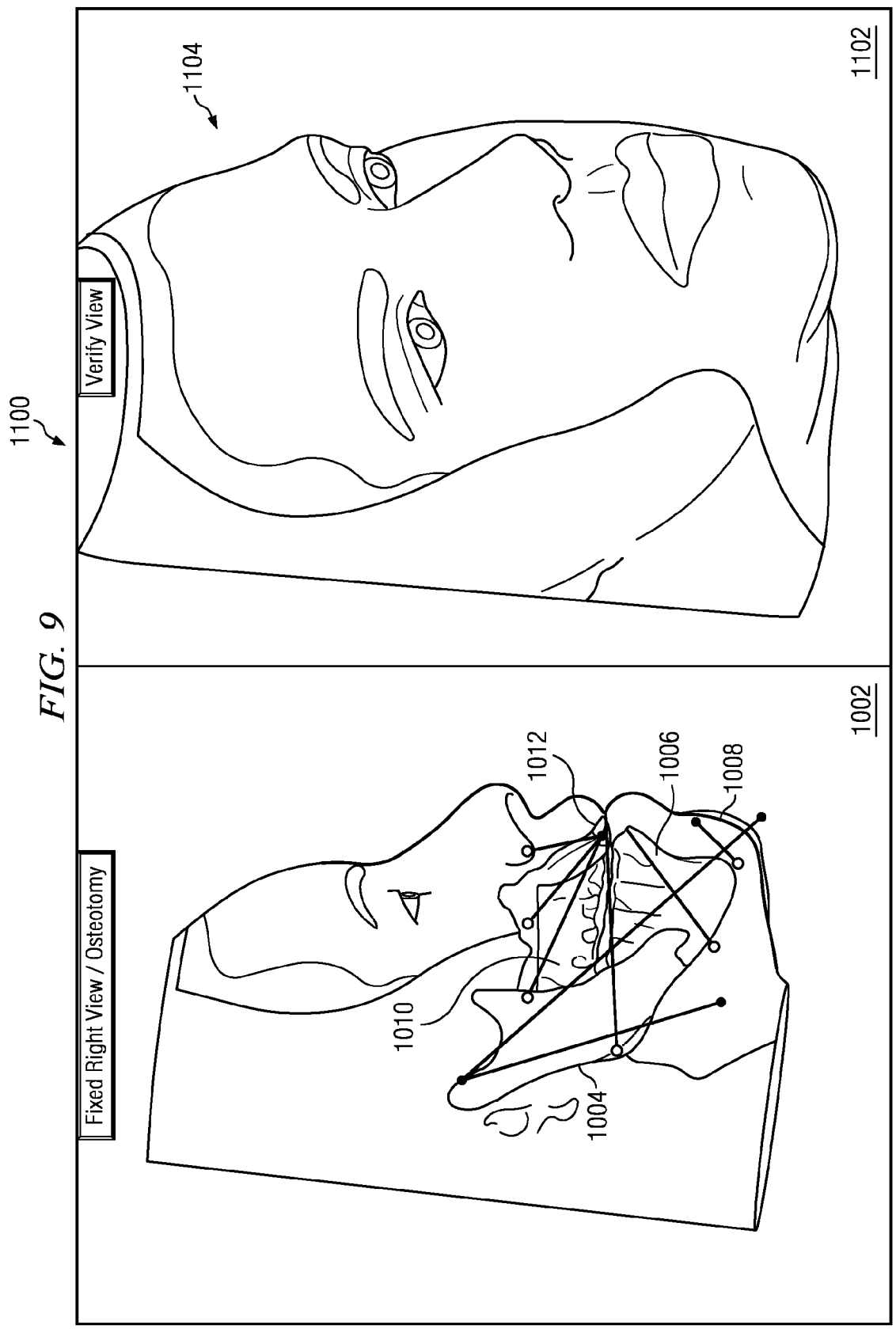

FIG. 9 depicts another example user interface screen 1100 of a computer-aided surgical planning tool that may be used in connection with osteotomy planning, in accordance with embodiments of the present disclosure. As shown in FIG. 9, user interface screen 1100 may include one or more panes 1002 depicting a two-dimensional view of a patient's cranio-facial features, including bony tissue and soft tissue, and a pane 1102 having a user-rotatable three-dimensional image 1104 depicting a patient's soft tissues and/or superficial facial features. Initially, image 1104 may be created based on a radiograph or other medical image of a patient's external soft tissue and a photograph or other image of the patient's superficial facial features overlaid and contoured to the external soft tissue.

A user may interact with user interface screen 1100 (e.g., using a keyboard, mouse, and/or other user input device) to simulate movement (e.g., translation or rotation) of a portion of a patient's bony tissue, and in response, the computer-aided surgical planning tool may redraw one or more of the two-dimensional images in panes 1002 to show the movement of such portion of bony tissue and simulate response of patient soft tissue to the movement, as well as redraw image 1104 to simulate response of patient soft tissue and superficial facial features to the movement. In addition, the user may interact with user interface screen 1100 (e.g., using a keyboard, mouse, and/or other user input device) to rotate image 1104 in pane 1102 to obtain varying perspectives of image 1104 to evaluate the effect of osteotomy movements on a patient's outward appearance. Thus, user interface 1100 may advantageously allow a user the ability to simulate movements in fixed, two-dimensional views, while viewing the patient response in a rotatable three-dimensional image.

Figure 10:
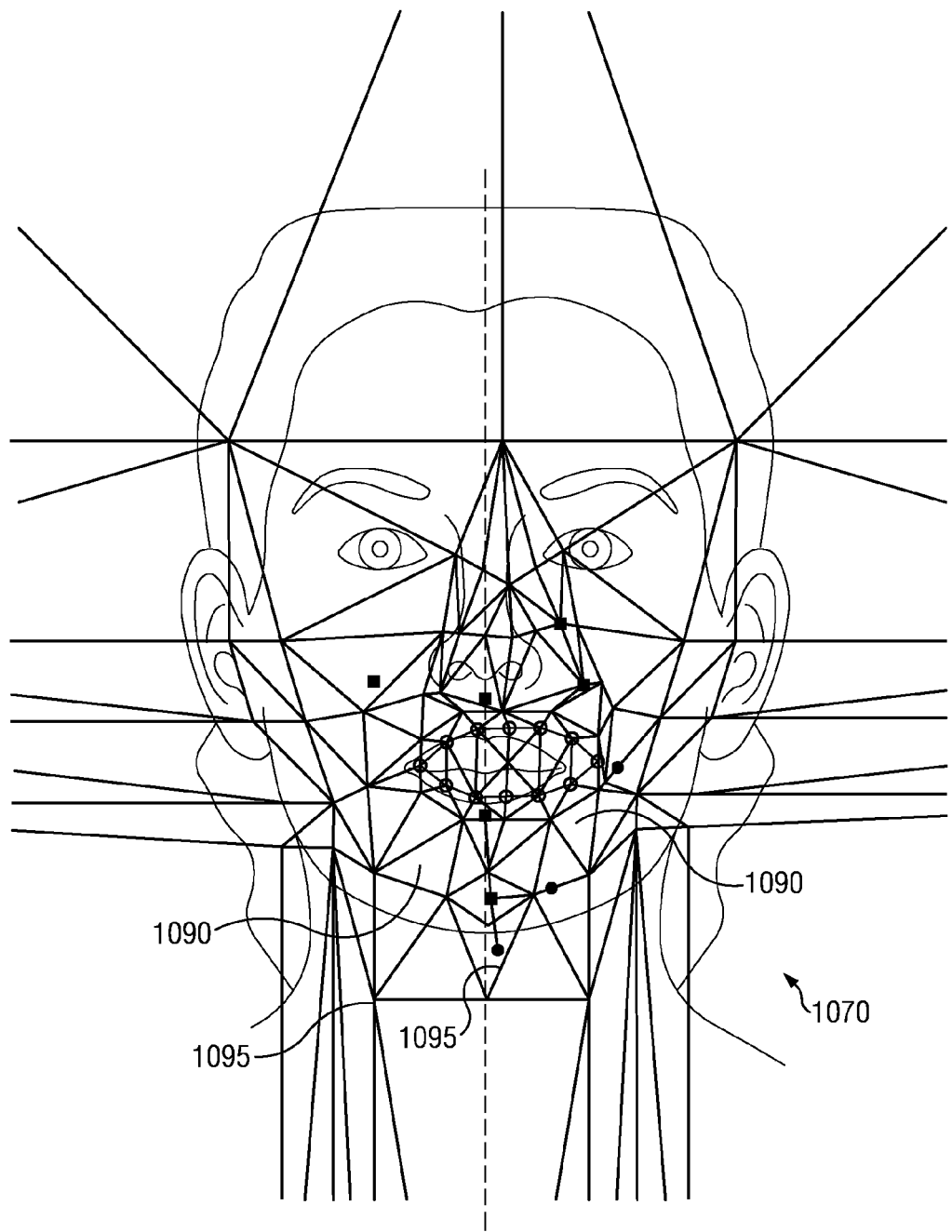
FIGS. 10 and 11 depict two-dimensional frontal view and right-side view images of a patient with various polygons and control points overlaid upon the images for use in modifying the images in response to simulated movement of bony tissue.
Figure 11:
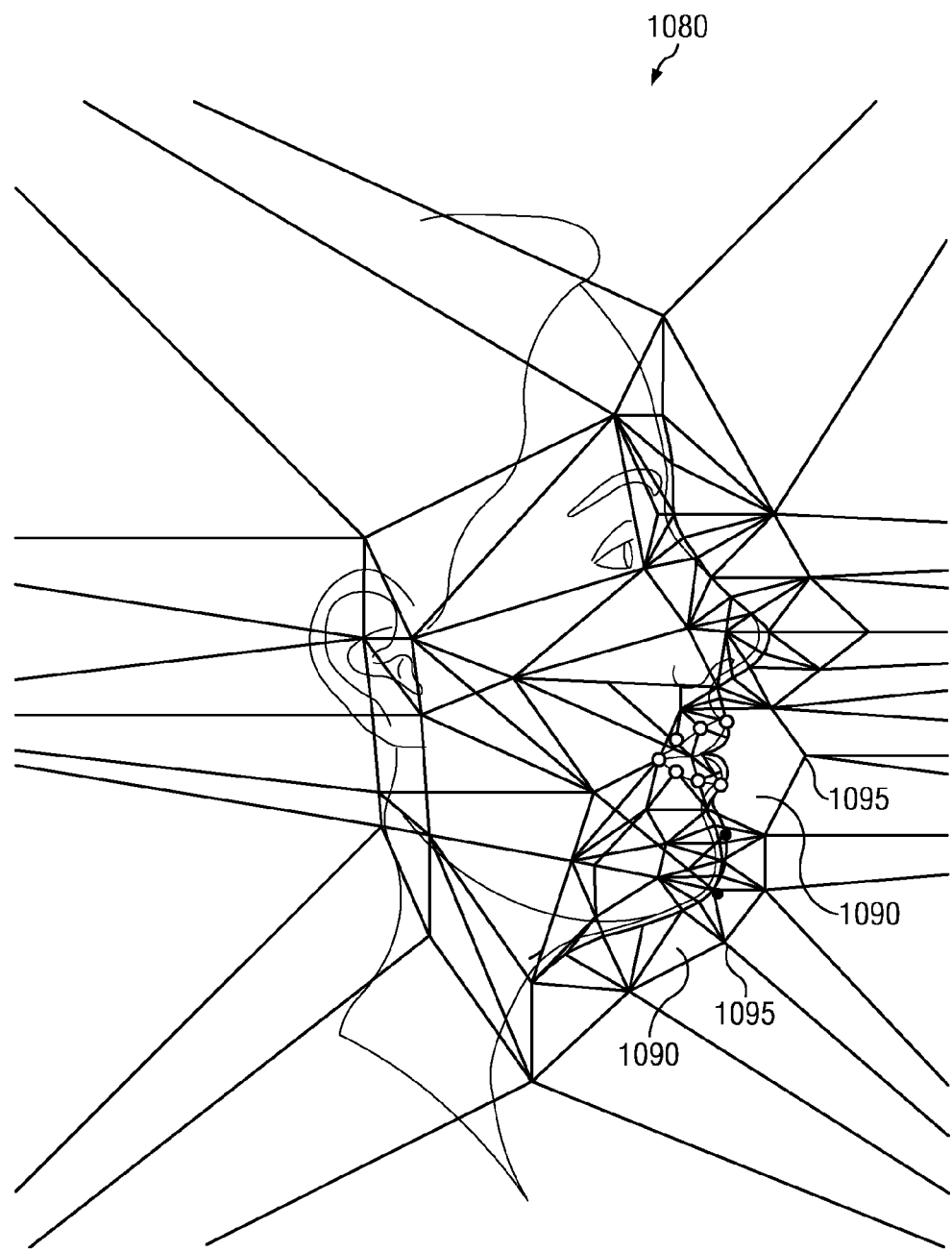

The computer-aided surgical planning tool may redraw based on simulated movement of bony tissue using any suitable approach. FIGS. 10 and 11 illustrate such an approach. FIGS. 10 and 11 depict a two-dimensional frontal view image 1070 and a two-dimensional right-side view image 1080 (as may be displayed in panes 1002) of a patient with various polygons 1090 and control points 1095 overlaid upon the images for use in modifying the images in response to simulated movement of bony tissue. In some embodiments, as shown in FIGS. 10 and 11, for each two-dimensional view of a patient (e.g., frontal view, left view, right view, etc.), a series of polygons 1090 (e.g., triangles) may be defined (e.g., either by a user of the computer-aided surgical planning tool or by algorithms of the computer-aided surgical planning tool recognizing features of a patient's face), each polygon 1090 defining a region of the patient's face in the particular view. The vertices of such polygons 1090 may serve as control points 1095. The polygons and vertices may not actually appear to a user during surgical simulation, but rather may exist as a logical construct to be used by the computer-aided surgical planning tool to mathematically and/or algorithmically modify patient images.

When a user of the computer-aided surgical planning tool simulates a movement of bony tissue, each control point 1095 may be translated based on its proximity to the portion of underlying bony tissue being moved and the degree to which the underlying bony tissue was moved. For example, for a simulated movement of a chin bone, control points 1095 proximate to the patient's chin may be translated by a greater distance than control points 1095 proximate to the patient's lips. In addition, the various pixels of the two-dimensional images and three-dimensional images of may be translated, redrawn, and displayed user interface screen 1100 based on such pixel's proximity to translated control points 1095 and the degree to which the control points 1095 were translated.

FIG. 12 depicts a block diagram of an example computing system 1200, in accordance with embodiments of the present disclosure. Computing system 1200 may be used in whole or part to provide or perform various functions and operations described above with respect to FIGS. 1-8. As shown in FIG. 12, computing system 1200 may include processor 1202, memory 1204, and logic 1206.

Computing system 1200 may comprise any suitable combination of hardware and/or software implemented in one or more modules to provide or perform the functions and operations described above with respect to FIGS. 1-11. In some embodiments, computing system 1200 may comprise a mainframe computer, general-purpose personal computer (PC), a Macintosh, a workstation, a Unix-based computer, a server computer, or any suitable processing device. In some embodiments, the functions and operations described above may be performed by a pool of multiple computing systems 1200.

Memory 1200 may comprise any suitable arrangement of random access memory (RAM), read only memory (ROM), magnetic computer disk, CD-ROM, or other magnetic, optical or solid state storage media, or any other volatile or nonvolatile memory devices that store one or more files, lists, tables, or other arrangements of information. Although FIG. 12 illustrates memory 1204 as internal to computing system, it should be understood that memory 1204 may be internal or external to computing system 1200, depending on particular implementations. Memory 1204 may be separate from or integral to other memory devices to achieve any suitable arrangement of memory devices for use in providing or performing desired operations or functionality.

Memory 1204 may be further operable to store logic 1206. Logic 1206 generally comprises rules, algorithms, code, tables, and/or other suitable instructions executable by processor 1202 to provide or perform the functions and operations described above with respect to FIGS. 1-11.

Memory 1204 may be communicatively coupled to processor 1202. Processor 1202 may be generally operable to execute logic to perform operations described herein. Processor 1202 may comprise any suitable combination of hardware and software implemented in one or more modules to provide the described function or operation.

Although the present disclosure has been described in detail, it should be understood that various changes, substitutions, and alterations can be made hereto without departing from the spirit and the scope of the invention as defined by the appended claims.

What is claimed is:

1. A method comprising:
    displaying one or more interactive two-dimensional images, each two-dimensional image representing at least bony tissue cranio-facial features of a patient and each two-dimensional image having one or more portions each associated with a corresponding portion of the patient's bony tissue such that a user may, via a user input device, cause movement of at least one of the one or more portions of such two-dimensional image to simulate movement of the corresponding portion of the patient's bony tissue in an osteotomy procedure;
    displaying a three-dimensional image representing exterior soft-tissue cranio-facial features of the patient;
    receiving input from a user regarding movement of a particular portion of the one or more portions of the two-dimensional image; and
    redrawing the three-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image;
    wherein at least one of the one or more two-dimensional interactive images are generated by:
        mapping an ellipse with its center at the origin of an xy-coordinate plane to a circle with its center at the origin of the xy-coordinate plane;
        transforming a three-dimensional subject image including a curved profile in the xy-coordinate plane to an intermediate image based at least on the mapping of the ellipse to the circle; and
        transforming the intermediate image to at least one of the one or more two-dimensional interactive images by distorting each of one or more points of interest of the intermediate image based at least on a dimension of the circle and a coordinate of such point.

2. A method according to claim 1, wherein the exterior soft-tissue cranio-facial features of the patient include superficial features of the patient's face.

3. A method according to claim 1, wherein movement of a particular portion of a patient's bony tissue includes at least one of rotation and translation of the particular portion of bony tissue.

4. A method according to claim 1, wherein the one or more two-dimensional images also represent exterior soft-tissue cranio-facial features of the patient, the method further comprising redrawing the two-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image.

5. A method according to claim 1, wherein the bony tissue cranio-facial features include at least one of the maxilla and the mandible of the patient.

6. An article of manufacture comprising:
    a non-transitory computer-readable medium; and
    computer-executable instructions carried on the computer-readable medium, the instructions executable by one or more processors and configured to cause the one or more processors to:
        display one or more interactive two-dimensional images, each two-dimensional image representing at least bony tissue cranio-facial features of a patient and each two-dimensional image having one or more portions each associated with a corresponding portion of the patient's bony tissue such that a user may, via a user input device, cause movement of at least one of the one or more portions of such two-dimensional image to simulate movement of the corresponding portion of the patient's bony tissue in an osteotomy procedure;
        display a three-dimensional image representing exterior soft-tissue cranio-facial features of the patient;
        receive input from a user regarding movement of a particular portion of the one or more portions of the two-dimensional image; and
        redraw the three-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image;
    wherein the computer-executable instructions are further configured to generate at least one of the one or more two-dimensional interactive images, the generating instructions further comprising instructions configured to:
        map an ellipse with its center at the origin of an xy-coordinate plane to a circle with its center at the origin of the xy-coordinate plane;
        transform a three-dimensional subject image including a curved profile in the xy-coordinate plane to an intermediate image based at least on the mapping of the ellipse to the circle; and
        transform the intermediate image to at least one of the one or more two-dimensional interactive images by distorting each of one or more points of interest of the intermediate image based at least on a dimension of the circle and a coordinate of such point.

7. An article of manufacture according to claim 6, wherein the exterior soft-tissue cranio-facial features of the patient include superficial features of the patient's face.

8. An article of manufacture according to claim 6, wherein movement of a particular portion of a patient's bony tissue includes at least one of rotation and translation of the particular portion of bony tissue.

9. An article of manufacture according to claim 6, wherein the one or more two-dimensional images also represent exterior soft-tissue cranio-facial features of the patient, the instructions further configured to cause the one or more processors to redraw the two-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image.

10. An article of manufacture according to claim 6, wherein the bony tissue cranio-facial features include at least one of the maxilla and the mandible of the patient.

11. A computing system, comprising:
a processor; and
a memory communicatively coupled to the processor and having stored thereon a program of instructions configured to, when executed by the processor:
display one or more interactive two-dimensional images, each two-dimensional image representing at least bony tissue cranio-facial features of a patient and each two-dimensional image having one or more portions each associated with a corresponding portion of the patient's bony tissue such that a user may, via a user input device, cause movement of at least one of the one or more portions of such two-dimensional image to simulate movement of the corresponding portion of the patient's bony tissue in an osteotomy procedure;
display a three-dimensional image representing exterior soft-tissue cranio-facial features of the patient;
receive input from a user regarding movement of a particular portion of the one or more portions of the two-dimensional image; and
redraw the three-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image;
wherein the instructions are further configured to generate at least one of the one or more two-dimensional interactive images, the generating instructions further comprising instructions configured to:
map an ellipse with its center at the origin of an xy-coordinate plane to a circle with its center at the origin of the xy-coordinate plane;
transform a three-dimensional subject image including a curved profile in the xy-coordinate plane to an intermediate image based at least on the mapping of the ellipse to the circle; and
transform the intermediate image to at least one of the one or more two-dimensional interactive images by distorting each of one or more points of interest of the intermediate image based at least on a dimension of the circle and a coordinate of such point.

12. A computing system according to claim 11, wherein the exterior soft-tissue cranio-facial features of the patient include superficial features of the patient's face.

13. A computing system according to claim 11, wherein movement of a particular portion of a patient's bony tissue includes at least one of rotation and translation of the particular portion of bony tissue.

14. A computing system according to claim 11, wherein the one or more two-dimensional images also represent exterior soft-tissue cranio-facial features of the patient, the program of instructions further configured to cause the processor to redraw the two-dimensional image based at least on the movement of the particular portion of the two-dimensional image to simulate response of the exterior soft-tissue cranio-facial features of the patient to movement of a portion of the patient's bony tissue corresponding to the particular portion of the two-dimensional image.

15. A computing system according to claim 11, wherein the bony tissue cranio-facial features include at least one of the maxilla and the mandible of the patient.

* * * * *